(12) United States Patent
Shi

(10) Patent No.: US 9,284,282 B2
(45) Date of Patent: Mar. 15, 2016

(54) 1,2,3-TRIAZOLE BASED METAL-ORGANIC FRAMEWORK AS PHOTO-ACTIVE MATERIALS

(71) Applicant: Xiaodong Shi, Morgantown, WV (US)

(72) Inventor: Xiaodong Shi, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 14/314,325

(22) Filed: Jun. 25, 2014

(65) Prior Publication Data

US 2014/0371465 A1    Dec. 18, 2014

Related U.S. Application Data

(62) Division of application No. 13/068,489, filed on May 12, 2011, now Pat. No. 8,779,155.

(60) Provisional application No. 61/395,341, filed on May 12, 2010.

(51) Int. Cl.
    *C07D 249/06*    (2006.01)
(52) U.S. Cl.
    CPC .................................. *C07D 249/06* (2013.01)
(58) Field of Classification Search
    None
    See application file for complete search history.

(56) References Cited

U.S. PATENT DOCUMENTS 3,666,758 A    5/1972    Dorlars et al.

FOREIGN PATENT DOCUMENTS

DE    1917740    10/1970

OTHER PUBLICATIONS

Yan, W. et al., N-2-Aryl-1,2,3-Triazoles: A Novel Class of UV/Blue-Light-Emitting Fluorophores with Tunable Optical Properties, Chemistry, Chem Eur J., 2011, 5011-5018, vol. 17, Wiley-VCH Verlag GmbH & Co. KGaA, Weinheim.

*Primary Examiner* — Kamal Saeed
(74) *Attorney, Agent, or Firm* — Buchanan Ingersoll & Rooney PC; Craig G. Cochenour

(57) ABSTRACT

A TAF compound that can have substitutions on either of the two benzene rings and/or the C-5 position of the triazole to alter the properties of the TAF compound can be wherein X can be H, an aromatic group, a hetero aromatic group, an alkyl or any substituted alkyl group, ketone, aldyhyde, carboxylic acid derivatives; $Y^1$, $Y^2$, $Y^3$, $Y^4$, and $Y^5$ can be one or more of H, aromatic groups, hetero aromatic groups, alkyl or any substituted alkyl groups, ketone, aldyhyde, or carboxylic acid derivatives; and $Z^1$, $Z^2$, $Z^3$, $Z^4$ and $Z^5$ can be one or more of H aromatic groups, hetero aromatic groups, alkyl or any substituted alkyl groups, ketone, aldyhyde, or carboxylic acid derivatives. Included is a preparation of the TAF compound and use as a photoactive and/or catalyst.

20 Claims, 2 Drawing Sheets

1,2,3-TRIAZOLE BASED METAL-ORGANIC FRAMEWORK AS PHOTO-ACTIVE MATERIALS

CROSS-REFERENCE TO RELATED APPLICATIONS

This utility patent application is a divisional patent application of and claims the benefit of priority of co-pending U.S. patent application Ser. No. 13/068,489, filed on May 12, 2011, which claims the benefit of priority of U.S. Provisional Application No. 61/395,341, filed on May 12, 2010.

REFERENCE TO SEQUENCE LISTING, A TABLE, OR A COMPUTER PROGRAM LISTING COMPACT DISC APPENDIX

Not Applicable

DETAILED DESCRIPTION OF THE INVENTION

A first embodiment can be triazole-modified compound TAF. The TAF compound can have substitutions on either of the two benzene rings and/or the C-5 position of the triazole to alter the properties of the TAF. The TAF compound can be

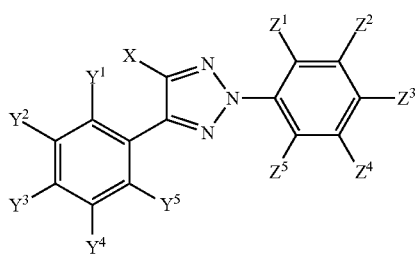

wherein X can be H, an aromatic group, a hetero aromatic group, an alkyl or any substituted alkyl group, ketone, aldyhyde, carboxylic acid derivatives; $Y^1$, $Y^2$, $Y^3$, $Y^4$, and $Y^5$ can be one or more of H, aromatic groups, hetero aromatic groups, alkyl or any substituted alkyl groups, ketone, aldyhyde, or carboxylic acid derivatives; and $Z^1$, $Z^2$, $Z^3$, $Z^4$ and $Z^5$ can be one or more of H aromatic groups, hetero aromatic groups, alkyl or any substituted alkyl groups, ketone, aldyhyde, or carboxylic acid derivatives.

TAF can be prepared from bifunctional 1,2,3-triazoles by treatment with $Zn(NO_3)_2$. About 1-5 mmol of the 1,2,3-triazole solutions wherein the solvents can be water, acetonitrile, DMSO, DMF, DEF, any alcohol, THF. This solution can be added to about 1-5 mmol $Zn(NO_3)_2$ solutions at a concentration between about 0.1 mmol to about 2 mol wherein the solvents can be water, acetonitrile, DMSO, DMF, DEF, any alcohol, THF. The solutions can be kept at an effective temperature which can range from about room temperature to about 180° C. for an effective time from about 1 hour to about 7 days to prepare TAF.

Figure 2:
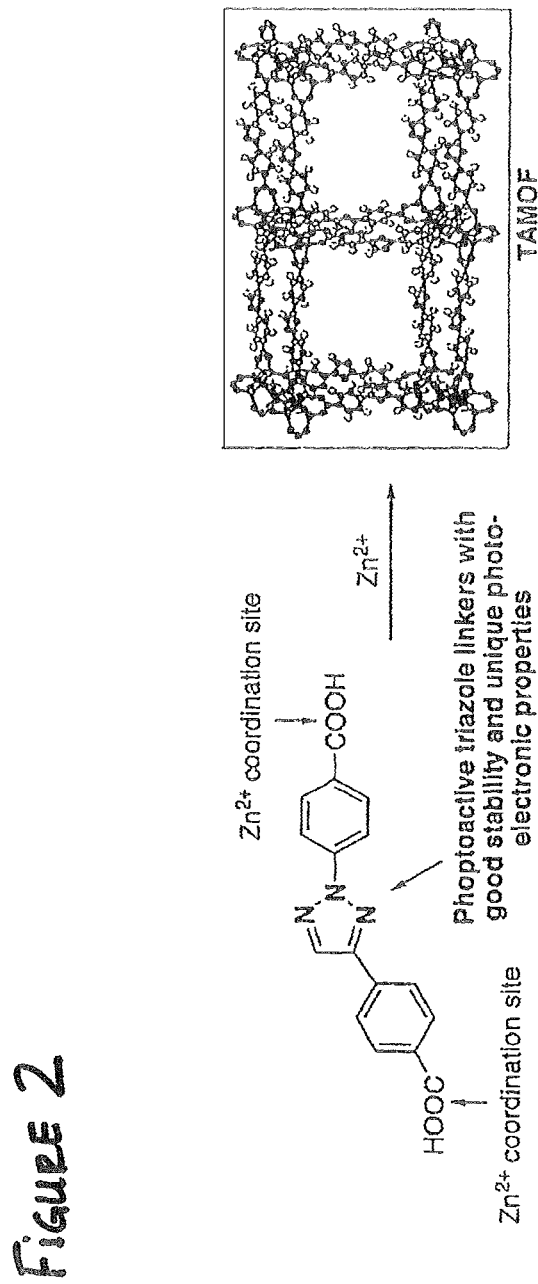
FIG. 2 is the reaction for TAMOF production.

FIG. 2 details the TAMOF preparation.

Figure 1:
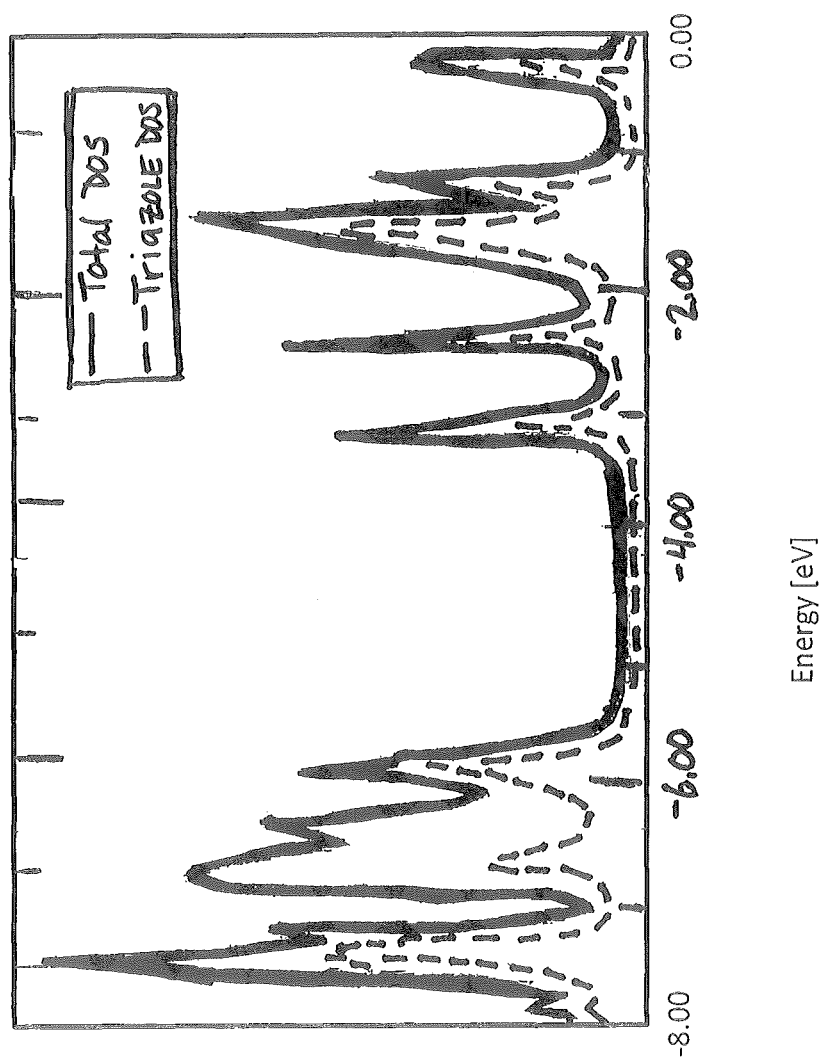
FIG. 1 is a representative structure of the ligand design and modification.

The TAF compound can be used as a photoactive material and/or catalyst. The absorption wavelength could be easily adjusted by the substitution of different aryl groups such as F, CN, Cl, OMe, phenyl, or heteroaromatic structures on the TAF compound. The N-aryl triazoles possess unique molecular orbital distributions. This feature makes the preparation of solar-light absorbing linkers for the preparation of metal-organic frameworks feasible. The orbital distribution made triazole one unique compound to express interesting photo and electronic properties. TAF has a band gap around 2.8 eV which is optimal for a photocatalysis as seen in FIG. 1. The HOMO and LUMO were confirmed locating on the triazole ring and H-bonding between C-4-H and $CO_2$ was revealed with a calculated 17 kcal/mol of binding energy.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

What is claimed is:

1. A method comprising preparing a compound of the formula:

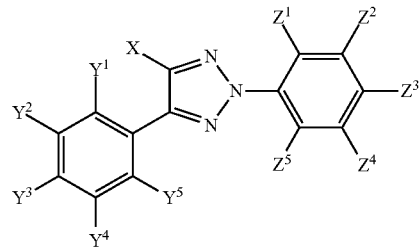

from bifunctional 1,2,3-triazoles with $Zn(NO_3)_2$ treatment wherein about 1-5 mmol of the bifunctional 1,2,3-triazoles in solution can be added to about 1-5 mmol of $Zn(NO_3)_2$ in solution at wherein the $Zn(NO_3)_2$ can be between about 0.1 mmol to about 2 mol in concentration wherein the solvents for the bifunctional 1,2,3-triazoles and the $Zn(NO_3)_2$ can be one or more of water, acetonitrile, dimethyl sulfoxide, dimethylformamide, diethylformamide, an alcohol, and tetrahydrofuran and the solutions are kept at an effective temperature for an effective time to prepare the compound of the formula:

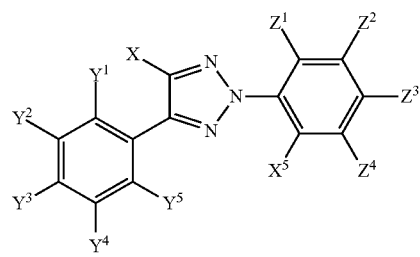

wherein X can be H, an aromatic group, a hetero aromatic group, an alkyl, any substituted alkyl group, ketone, aldyhyde, or carboxylic acid derivative, $Y^1$, $Y^2$, $Y^3$, $Y^4$, and $Y^5$ can be one or more of H, aromatic groups, hetero aromatic groups, alkyl, any substituted alkyl groups, ketone, aldyhyde, or carboxylic acid derivative, and $Z^1$, $Z^2$, $Z^3$, $Z^4$ and $Z^5$ can be one or more of H, aromatic groups, hetero aromatic groups, alkyl, any substituted alkyl groups, ketone, aldyhyde, or carboxylic acid derivative.

2. The method of claim 1 wherein the effective temperature is from about room temperature to about 180° C.

3. The method of claim 1 wherein the effective time is from about 1 hour to about 7 days.

4. The method of claim 2 wherein the effective time is from about 1 hour to about 7 days.

5. The method of claim 1, wherein when $Y^3$ is COOH then $Z^3$ is other than COOH, and wherein $Z^3$ is COOH then $Y^3$ is other than COOH.

6. The method of claim 5 wherein the effective temperature is from about room temperature to about 180° C.

7. The method of claim 5 wherein the effective time is from about 1 hour to about 7 days.

8. The method of claim 6 wherein the effective time is from about 1 hour to about 7 days.

9. The method of claim 5, wherein $Y^3$ is COOH and $Z^3$ is other than COOH.

10. The method of claim 9 wherein the effective temperature is from about room temperature to about 180° C.

11. The method of claim 9 wherein the effective time is from about 1 hour to about 7 days.

12. The method of claim 10 wherein the effective time is from about 1 hour to about 7 days.

13. The method of claim 5, wherein $Z^3$ is COOH and $Y^3$ is other than COOH.

14. The method of claim 13 wherein the effective temperature is from about room temperature to about 180° C.

15. The method of claim 13 wherein the effective time is from about 1 hour to about 7 days.

16. The method of claim 14 wherein the effective time is from about 1 hour to about 7 days.

17. The method of claim 1, wherein X is H, $Y^1$, $Y^2$, $Y^4$, and $Y^5$ are each H, $Z^1$, $Z^2$, $Z^4$ and $Z^5$ are each H, and $Y^3$ and $Z^3$ are each COOH.

18. The method of claim 17 wherein the effective temperature is from about room temperature to about 180° C.

19. The method of claim 17 wherein the effective time is from about 1 hour to about 7 days.

20. The method of claim 18 wherein the effective time is from about 1 hour to about 7 days.

\* \* \* \* \*